United States Patent [19]

Coburn et al.

[11] Patent Number: 5,281,706

[45] Date of Patent: Jan. 25, 1994

[54] SYNTHESIS OF 3,6-DIAMINO-1,2,4,5-TETRAZINE

[75] Inventors: Michael D. Coburn; Donald G. Ott, Los Alamos, both of N. Mex.

[73] Assignee: The United States of America as represented by the United States Department of Energy, Washington, D.C.

[21] Appl. No.: 980,892

[22] Filed: Nov. 24, 1992

[51] Int. Cl.$^5$ .......................................... C07D 257/08
[52] U.S. Cl. .................................................. 544/179
[58] Field of Search ........................................ 544/179

[56] References Cited

PUBLICATIONS

Michael D. Coburn et al., "An Improved Synthesis of 3,6-Diamino-1,2,4,5-Tetrazine. I", J. Heterocyclic Chem., 27, pp. 1941-1945 (1990).

M. D. Coburn et al., "An Improved Synthesis of 3,6-Diamino-1,2,4,5-Tetrazine. II From Triaminoguanidine and 2,4-Pentanedione", J. Heterocyclic Chem., 28, pp. 2049-2050 (1991).

Chao-Han Lin et al., "The Synthesis of sym-Diaminotetrazine", J. Am. Chem. Soc., 76, pp. 427-430 (1954).

R. N. Butler et al., "Sequential Attack by a Diketone on a Polyhydrazine; The Reaction of Triaminoguanidine With Acetylacetone", J. Chem. Soc., (C), pp. 2510-2512 (1970).

*Primary Examiner*—John M. Ford
*Attorney, Agent, or Firm*—Richard J. Cordovano; Paul D. Gaetjens; William R. Moser

[57] ABSTRACT

A method of making 3,6-diamino-1,2,4,5-tetrazine.

6 Claims, 1 Drawing Sheet

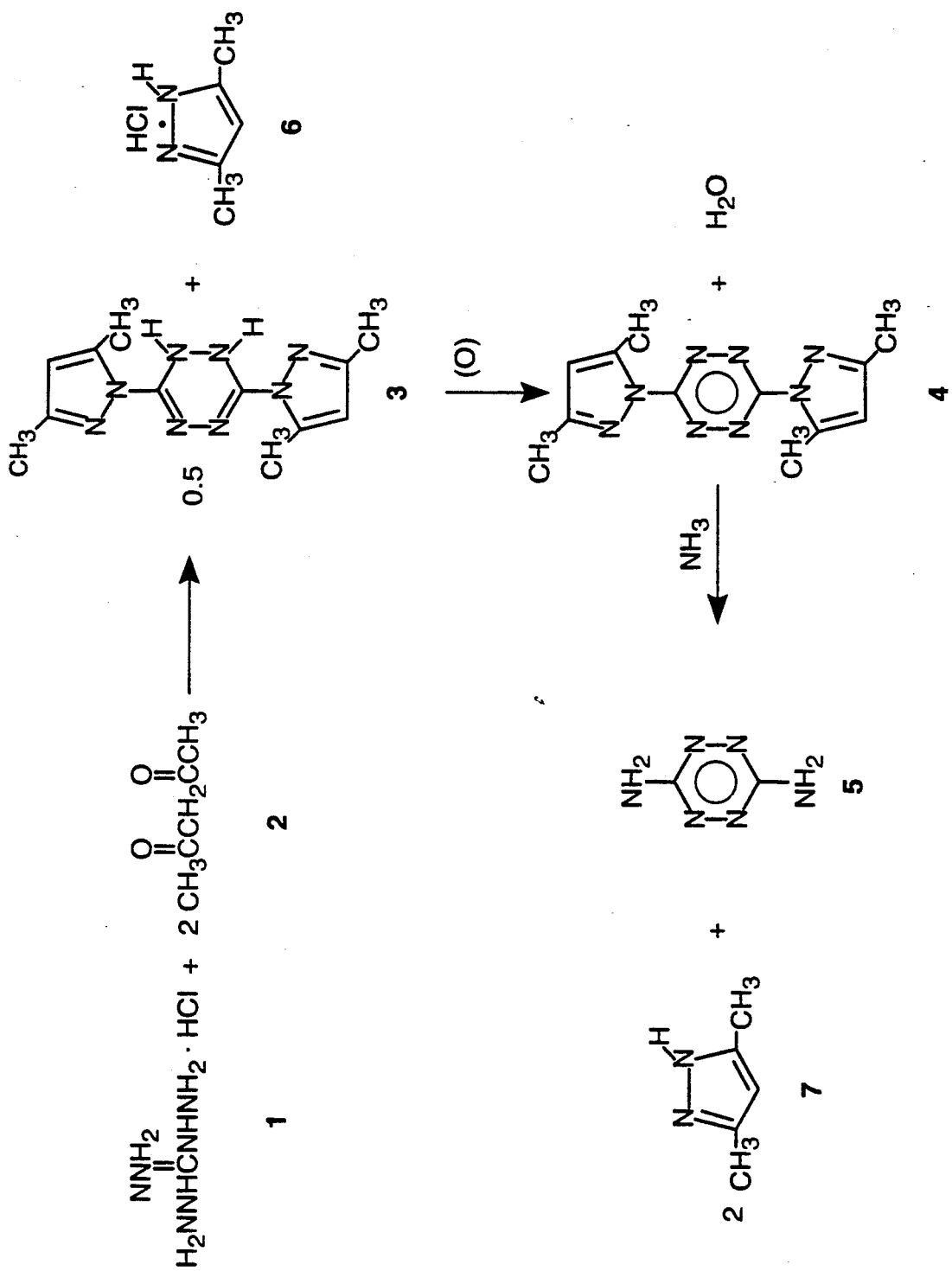

SYNTHESIS OF 3,6-DIAMINO-1,2,4,5-TETRAZINE

This invention is the result of a contract with the Department of Energy (Contract No. W-7405-ENG-36).

BACKGROUND OF THE INVENTION 3,6-Diamino-1,2,4,5,-tetrazine is useful as a precursor to 3,6-diamino-1,2,4,5,-tetrazine-1,4-dioxide, which is a new explosive currently being evaluated at Los Alamos National Laboratory. It is useful in a rocket fuel system which is described in U.S. Pat. No. 3,797,238 to Iwanciow issued Mar. 19, 1974 and as an antibiotic, as described in United Kingdom patent GB 1245443, dated Sep. 8, 1971.

SUMMARY OF THE INVENTION

This invention is a method of making 3,6-diamino-1,2,4,5,-tetrazine (compound 5, DATZ). Triaminoguanidine monohydrochloride (compound 1) in water solution is combined with 2,4-pentanedione (compound 2) to form a precipitate comprised of 3,6-bis(3,5-dimethylpyrazol-1-yl)-1,2-dihydro-1,2,4,5-tetrazine (compound 3). A mixture of compound 3 in a suitable solvent is contacted with nitric oxide (NO) or nitrogen dioxide ($NO_2$) to form 3,6-bis(3,5-dimethylpyrazol-1-yl)-1,2,4,5-tetrazine (compound 4). The NO or $NO_2$ is then removed from the mixture by passing an inert gas through the mixture or, alternatively, compound 4 is separated from the mixture and mixed with fresh solvent to form a mixture free of NO and $NO_2$. The mixture is contacted with ammonia ($NH_3$), first at a temperature below about 35 C and then at a temperature above about 50 C, to form 3,6-diamino-1,2,4,5-tetrazine and 3,5-dimethyl-1H-pyrazole (compound 7). A preferred solvent is 1-methyl-2-pyrrolidinone (NMP).

SUMMARY OF THE INVENTION

The Drawing depicts a sequence of chemical reactions, using structural formulas, which is believed to occur when carrying out the steps of the invention. The compound numbers are correlated with compound names in the above paragraph.

DETAILED DESCRIPTION OF THE INVENTION

There are several methods which may be used by one skilled in the art to synthesize compound 1. Following is an example of the method used by the present inventor.

EXAMPLE 1

34.1 g of hydrazine monohydrate was added to a slurry consisting of 19.1 g of guanidine hydrochloride in 100 ml of 1,4-dioxane. The mixture was stirred and heated to a temperature of about the boiling point of 1,4-dioxane for about 2 hours, using a reflux condenser to prevent loss of material. Then, the mixture was allowed to cool and filtered. The solid material from the filtration step was washed with 1,4-dioxane, dried, and identified as 27.7 g of pure compound 1.

Other suitable organic solvents, such as 1-propanol, may be used in place of 1,4-dioxane. When water was used as the solvent, the yield of compound 1 was poor. The reactants were purchased from the Aldrich Chemical Company.

Compound 3 was made in the manner illustrated by the following example.

EXAMPLE 2

10.0 g of compound 2 was added in a dropwise manner to a solution consisting of 7.03 g of compound 1 in 50 ml of water at room temperature. The temperature of the mixture rose during addition of compound 2. The amount of compound 2 added was the stoichiometric amount needed to completely react with compound 1. The mixture was stirred for about 0.5 hours and then heated and stirred at 70 C for about 4 hours, during which time a solid precipitated from the solution. The solid was filtered from the mixture after the mixture cooled, washed with water, dried, and identified as 5.77 g of pure compound 3. The yield was 85%.

The conditions of Example 2 are believed to be optimum. The reaction will take place slowly at room temperature and yields appear to be less at temperatures above 70 C. The reaction was run in 1-propanol, in which compound 2 is slightly soluble, but yields were not as large as when water was used as the reaction medium. Yield when using 1-propanol was increased by adding a small amount of water to the reaction mixture. A one pot process may be used to make compounds 1 and 3. Solvent is distilled off from the mixture of solvent and compound 1, then water is added, and then compound 2 is added.

Oxidation of compound 3 to compound 4 using gaseous oxygen in 1,4-dioxane, in sulfolane, in 1,2-dichloroethane, and in NMP was investigated. At room temperature, the reaction was found to be faster in NMP than in the other solvents, but was still very slow. At 90 C in NMP using $O_2$, the reaction was complete in 0.5 hour, but significant amounts of by-products were formed. These by-products were also found in lesser amounts in the reactions run at room temperature.

NO and $NO_2$ were found to be effective in converting compound 3 to compound 4. A gas may be bubbled through a mixture of compound 3 in a suitable solvent or the NO or $NO_2$ may be contacted with the mixture in a pressure reactor. For example, a 0.5 molar mixture of compound 3 in NMP was placed in a pressure reactor with an excess of NO above it at 50 psig for 1 hour at room temperature, resulting in complete conversion to compound 4 with no trace of by-products. 70% conversion to compound 4 was obtained when a 1.0 molar slurry of compound 3 was contacted with an equimolar amount of $NO_2$. Complete conversion was obtained when 2 molar equivalents of $NO_2$ were used. A suitable solvent is an organic solvent in which compound 3 is at least slightly soluble and which does not react with the components of the mixture. A substance which is slightly soluble in a solvent will generally have a solubility of at least about one gram per liter of solvent. Examples of suitable solvents are NMP, toluene, formamide, and dimethylformamide. NMP is a preferred solvent. Following are illustrative examples.

EXAMPLE 3

A slurry consisting of 6.8 g of compound 3 and 50 ml of NMP at room temperature was placed in a gas washing bottle having a glass frit gas dispersion tube at its bottom. Nitric oxide in gaseous form from a storage cylinder was passed into the slurry through the dispersion tube at a rate of 500 ml/minute for 1 hour. Then the mixture was poured into 200 ml of ice water and the resulting mixture filtered to isolate a red solid. The solid was washed with water, dried, and identified as 6.7 g of pure compound 4. The yield was 99%.

EXAMPLE 4

A slurry consisting of 13.6 g of compound 3 and 50 ml of NMP at room temperature was placed in a gas washing bottle having an open-ended gas dispersion tube extending to its bottom. $NO_2$ in gaseous form was passed into the rapidly-stirred slurry through the tube. The gas could not be passed into the slurry by means of glass frit due to plugging of the frit. 3.2 ml of liquid $NO_2$ was vaporized and contacted with the slurry in a period of 5 or 10 minutes. Pure compound 4 in an amount of 13.3 g was then separated from the mixture. The yield was 99%.

Compound 4 is converted to compound 5 and 3,5-dimethyl-1H-pyrazole (compound 7) by ammonolysis. Gaseous ammonia is contacted with a mixture of compound 4 and a suitable solvent, such as NMP (which is preferred), toluene, dimethylformamide, or formamide. The reaction may be carried out by placing the mixture in a pressure reactor and then pressurizing with $NH_3$ or by other methods which provide contact between $NH_3$ and the mixture. Compound 4 must be at least slightly soluble in the solvent and the solvent must not react with the components of the mixture. In general, chlorinated solvents, esters, and ketones will not be suitable, as they will react with $NH_3$. It is necessary that the mixture and ammonia be initially contacted at a temperature below about 35 C and that the temperature then be increased to above about 50 C. Experiments were accomplished in which the mixture was contacted with $NH_3$ at room temperature and then the balance of the ammonolysis procedure was carried out at about 90 C, resulting in about 70% conversion after about 4 hours with complete conversion to compound 5 taking about 6 hours. Complete conversion required about 7 hours when the temperature was increased only to 70 C. When ammonolysis is carried out entirely at room temperature, 3-amino-6-(3,5-dimethylpyrazol-1-yl)-1,2,4,5-tetrazine (compound 8) is formed. This reaction proceeds rapidly. It is believed that a temperature below about 35 C is required for the ammonolysis of compound 4 to compound 8 to result in substantially complete conversion and that a temperature above about 50 C (after initial ammonolysis at below 35 C) is required for the reaction of compound 4 to compound 5 to take place at a reasonable rate. Those skilled in the art will appreciate the interplay of time and temperature in regard to the relative amounts of compounds 5 and 8 which are formed. In synthesizing compound 5, it is desirable that $NH_3$ be present in an amount greater than the stoichiometric requirement, since the reaction kinetics are such that the ammonolysis takes place slowly when only stoichiometric amounts are present. It is preferred to provide $NH_3$ in excess by a factor of 3 or more. Following is an illustrative example.

EXAMPLE 5

A 100 ml capacity pressure reactor was charged with a mixture of 13.5 g of compound 4 and 50 ml of NMP. 5 g of $NH_3$ gas from a storage cylinder was added to the space above the mixture over a period of about 30 minutes with no heating. The pressure in the reactor was about 60 psig. The contents of the reactor were then heated to about 90 C and the pressure rose to about 150 psig. After 6 hours with stirring by the magnetic stirrer with which the reactor was equipped, the mixture was allowed to cool to room temperature and 100 ml of 2-propanol was added to the mixture to enhance precipitation of compound 5. After the mixture stood overnight to allow complete precipitation, the precipitate was separated by filtration, washed with 2-propanol, and dried. The dry precipitate consisted of 5.6 g of pure compound 5.

Oxidation and ammonolysis may be accomplished without isolating compound 4 from the solvent containing compound 4 and NO or $NO_2$ if the gas used for oxidation is removed from the reaction mixture before addition of ammonia. This may be done by purging with a gas which is inert with respect to the reaction mixture, such as air or nitrogen. Following is an illustrative example.

EXAMPLE 6

A mixture of 13.6 g of compound 3 in 50 ml of NMP was contacted with 0.10 mole of $NO_2$ as described in Example 4. Then, nitrogen was bubbled through the mixture for about 10 minutes. The mixture was then transferred to a pressure reactor and contacted with 5 g of $NH_3$ at about 90 C as described in Example 5. The amount of pure compound 5 which was recovered was 5.38 g. The yield was 96%.

Compounds were identified by means of carbon-13 and nitrogen-15 nuclear magnetic resonance spectroscopy and elemental (combustion) analysis.

This invention is described in a paper entitled "An Improved Synthesis of 3,6-Diamino-1,2,4,5-tetrazine", which appeared in the Journal of Heterocyclic Chemistry, vol. 28. page 2049 (December 1991). This paper is incorporated in full into this patent application.

The above examples are intended to be illustrative only and are not intended to constitute an undue limitation on the broad scope of the claims. Modifications and variations will be apparent to those skilled in the art.

We claim:

1. A process for making 3,6-diamino-1,2,4,5-tetrazine which comprises:
   a. combining a solution of triaminoguanidine monohydrochloride in water with 2,4-pentanedione to form a precipitate and recovering said precipitate;
   b. forming a first mixture of the precipitate and a suitable solvent;
   c. contacting said first mixture with nitric oxide or nitrogen dioxide;
   d. separating a solid fraction from said first mixture and mixing said solid fraction with a suitable solvent to form a second mixture;
   e. contacting said second mixture with ammonia at a temperature below about 35 C and then at a temperature above about 50 C; and
   f. recovering 3,6-diamino-1,2,4,5-tetrazine from the second mixture.

2. The process of claim 1 where said triaminoguanidine monohydrochloride is synthesized by reacting guanidine hydrochloride and hydrazine monohydrate in a non-aqueous liquid.

3. The process of claim 1 where said solvent is 1-methyl-2-pyrrolidinone.

4. A process for making 3,6-diamino-1,2,4,5,-tetrazine which comprises:
   a. combining a solution of triaminoguanidine monohydrochloride in water with 2,4-pentanedione to form a precipitate and recovering said precipitate;
   b. forming a mixture of the precipitate and a suitable solvent;

c. contacting said mixture with nitric oxide or nitrogen dioxide;

d. passing an inert gas through the mixture to remove said nitric oxide or said nitrogen dioxide;

e. contacting the mixture with ammonia at a temperature below about 35 C and then at a temperature above about 50 C; and f. recovering 3,6-diamino-1,2,4,5,-tetrazine from the mixture.

5. The process of claim 4 where said triaminoguanidine monohydrochloride is synthesized by reacting guanidine hydrochloride and hydrazine monohydrate in a non-aqueous liquid.

6. The process of claim 4 where said solvent is 1-methyl-2-pyrrolidinone.

* * * * *